US012558056B2

(12) United States Patent
Kuenen et al.

(10) Patent No.: US 12,558,056 B2
(45) Date of Patent: Feb. 24, 2026

(54) ULTRASOUND BASED BLOOD FLOW VELOCITY MEASUREMENTS

(71) Applicant: KONINKLIJKE PHILIPS N.V., Eindhoven (NL)

(72) Inventors: Maarten Petrus Joseph Kuenen, Veldhoven (NL); Brian Brand Antonius Johannes Bloemendal, Helenaveen (NL); Lucas Hendrikus Gerardus Tan, Vosselaar (BE); Patrick Wilhelmus Van Kaam, Best (NL); Johan Thomas Oostveen, Eindhoven (NL); Peter Alexander Barendse, Helmond (NL); Franciscus Paulus Maria Budzelaar, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 95 days.

(21) Appl. No.: 18/709,702

(22) PCT Filed: Nov. 10, 2022

(86) PCT No.: PCT/EP2022/081380
§ 371 (c)(1),
(2) Date: May 13, 2024

(87) PCT Pub. No.: WO2023/088760
PCT Pub. Date: May 25, 2023

(65) Prior Publication Data
US 2025/0000481 A1     Jan. 2, 2025

(30) Foreign Application Priority Data

Nov. 17, 2021   (EP) ..................................... 21208674
May 11, 2022   (EP) ..................................... 22172687

(51) Int. Cl.
A61B 8/06       (2006.01)
A61B 8/00       (2006.01)

(52) U.S. Cl.
CPC ................ A61B 8/06 (2013.01); A61B 8/461 (2013.01); A61B 8/488 (2013.01); A61B 8/5207 (2013.01); A61B 8/5269 (2013.01)

(58) Field of Classification Search
CPC ........... A61B 8/06; A61B 8/461; A61B 8/488; A61B 8/5207; A61B 8/5269; A61B 8/12; A61B 8/5223
See application file for complete search history.

(56) References Cited

U.S. PATENT DOCUMENTS 5,429,137  A  *   7/1995  Phelps .................... G01P 5/244
                                                          600/455
5,522,393  A  *   6/1996  Phillips ............... G01S 15/8984
                                                          600/455

(Continued)

FOREIGN PATENT DOCUMENTS

EP           3854310 A1     7/2021
WO      2021148416 A1     7/2021

OTHER PUBLICATIONS

International Search Report and Written Opinion of PCT/EP2022/081380, dated Feb. 6, 2023.

*Primary Examiner* — Bo Joseph Peng

(57) ABSTRACT

Improvements in ultrasound based blood flow velocity measurements are disclosed, including: suppressing interference components from the Doppler spectrum, in order to prevent them from affecting the flow measurements.

15 Claims, 9 Drawing Sheets

(56)     References Cited

U.S. PATENT DOCUMENTS

| | | | |
|---|---|---|---|
| 6,549,801 B1 * | 4/2003 | Chen .................... | G01B 9/0201 |
| | | | 250/350 |
| 8,366,624 B1 * | 2/2013 | Tamura .............. | G01S 15/8986 |
| | | | 600/455 |
| 8,435,182 B1 * | 5/2013 | Tamura ................. | A61B 8/488 |
| | | | 600/453 |
| 8,579,821 B1 * | 11/2013 | Tamura ............... | A61B 8/0883 |
| | | | 600/455 |
| 2004/0158155 A1 * | 8/2004 | Njemanze ........... | A61B 8/4227 |
| | | | 600/454 |
| 2012/0089027 A1 | 4/2012 | Andreuccetti | |
| 2012/0215110 A1 * | 8/2012 | Wilkening ............ | A61B 8/488 |
| | | | 600/453 |
| 2015/0141832 A1 | 5/2015 | Yu | |

* cited by examiner

ULTRASOUND BASED BLOOD FLOW VELOCITY MEASUREMENTS

CROSS-REFERENCE TO PRIOR APPLICATIONS

This application is the U.S. National Phase application under 35 U.S.C. § 371 of International Application No. PCT/EP2022/081380, filed on Nov. 10, 2022, which claims the benefit of European Patent Application No. 21208674.8, filed on Nov. 17, 2021 and European Patent Application No. 22172687.0, filed on May 11, 2022. These applications are hereby incorporated by reference herein.

I. SYSTEM AND METHOD FOR DETECTION AND SUPPRESSION OF ELECTROMAGNETIC INTERFERENCE IN INTRAVASCULAR DOPPLER FLOW MEASUREMENTS

Electromagnetic interference (EMI) can be a significant problem in intravascular Doppler flow measurements given that the disposable guidewire and cabling can operate as a receiving antenna for any interference sources present at or near the clinical site where the measurement is done. EMI may cause erroneous measurements, and if it is too big of a problem, it may prevent any valid measurements from being performed. We propose a system and method for differentiating between signal, noise, and interference components in Doppler flow spectra and for suppression of any interfering components. The approach is based on assessment of similarity among Doppler spectra measured over a range of depths.

I.1 BACKGROUND OF THE INVENTION

Assessing the hemodynamic significance of cardiovascular and peripheral vascular disease by intravascular flow measurement has been shown beneficial to guide treatment of circulatory disease. Especially, in the coronary arteries large clinical trials have proven that decision-making based on pressure and flow measurements improves clinical outcome compared to angiography alone. Flow measurements are particularly valuable in the case of non-obstructive coronary artery disease, i.e. angina complaints without visible obstructions in the large arteries. Additionally, beyond diagnostics, blood flow monitoring during embolization interventions is potentially helpful in assessing the degree of embolization and guiding when to stop to prevent embolization of healthy tissue, for example in transarterial chemoebolization (TACE).

To assess blood flow velocity, guide wires with a Doppler ultrasound sensor were developed more than two decades ago and are equipped with a single element lead zirconate titanate (PZT) ultrasound transducer. With these devices, an electrical driving pulse can be sent to the PZT which emits an ultrasound pulse and a reflected ultrasound pulse is received by the PZT, which is converted to electrical signal. By analysis of the difference between the sent and received signals, the blood velocity in a specific sampling area can be deduced as in standard ultrasound pulsed Doppler measurements (see FIG. 1).

At the moment, Philips Volcano is the only company that manufactures and sells Doppler ultrasound guidewires (FloWire and ComboWire) for blood velocity measurements in the coronary arteries.

FIG. 2 shows an example of the flow velocity that is determined based on measurements with the FloWire. The distribution of velocities in the sample area is shown in time as a grayscale image. One vertical line in the Doppler image describes the relative extent to which the velocity along the vertical axis is observed. The blue contour is the estimated instantaneous peak velocity (IPV) in the vessel at each point in time. In clinical practice, the average peak velocity (APV) is obtained by averaging the IPV over one or more cardiac cycles, and the APV is used as a surrogate for the flow.

I.2 PROBLEMS OR DISADVANTAGES OVERCOME BY THE INVENTION

With the increase in the number of various kinds of equipment and electronically tagged items (e.g. RF ID tags), the presence of electromagnetic interference in clinical environment has increased. These interferences degrade the quality of the ultrasound signal and the associated Doppler image that is derived from the ultrasound signal, and more importantly, disturb the estimation of the instantaneous peak velocity (IPV) and average peak velocity (APV). Therefore, the interferences may significantly influence and impact the clinical outcome or decisions based on Doppler flow measurements. For the intravascular Doppler flow measurement, this is especially problematic because of two factors:
1. the disposable interventional device, e.g. guidewire, and/or connector cable can act as a receiving antenna;
2. the measured signal is very small, e.g. in the order of u V range, and thus easily dominated by interference sources.

Owing to these factors, the design of acquisition electronics that is minimally sensitive to any electromagnetic interference (EMI) sources is of great importance. Even so, it is generally not possible to control the sources of EMI and therefore very difficult to guarantee that EMI will not affect the flow measurement. The problem addressed in this invention is the susceptibility of ultrasound-based flow measurement processing to interference sources, with particular focus on those interference sources that are deterministic.

In fact, in FIG. 2 we can see a clear example of interference that manifests itself as the bright white horizontal line near the top of the Doppler spectrum image, just above 90 cm/s. Had this line been positioned somewhat lower and partially overlaid with the flow signal component, this line would have complicated the IPV estimation and potentially caused erroneous measurements.

The object of the invention involves the insight that signal, noise, and interference components present in the Doppler spectrum can be differentiated by analysis of spectral statistics. Additionally, methodology is proposed to suppress interference components from the Doppler spectrum, in order to prevent them from affecting the flow measurements.

I.3 DETAILED DESCRIPTION OF HOW TO BUILD AND USE THE INVENTION

In a main embodiment, we propose to suppress interference components from the Doppler ultrasound flow velocity spectra. The system comprises:
  intravascular device (e.g. guidewire or catheter) with one or more ultrasound elements. The ultrasound element on the intravascular device may be any of PZT, capacitive micromachined ultrasound transducer (CMUT), piezoelectric micromachined ultrasound transducer (PMUT), polyvinilidene fluoride (PVDF) ultrasound transducer;

wired or wireless connection between intravascular device and acquisition and/or control electronics;

acquisition and/or control electronics (e.g. a console or a patient interface module (PIM) comprising at least a processor configured for at least one of an analog preprocessing, digitization, and means for digital processing of signals measured by intravascular device;

software, preferably running in real-time causing the at least one processor to carry out flow signal processing, but not excluding off-line processing, comprising at least:

flow velocity (Doppler) spectrum estimation (e.g. using pulsed-wave Doppler processing) over a range of depths;

detection and suppression of interference components from the Doppler flow spectrum based on a measure for similarity or variation.

The main element of the invention follows from understanding and application of metrics of similarity or variation, e.g. statistical or coherence measures, to spectrum data obtained over a range of depths in order to reduce interference. In this description we focus on three components in the Doppler spectrum: the desired flow signal, noise, and interference.

In the exemplary similarity metric detailed below, the focus is on first and second-order statistics (i.e., mean, variance and standard deviation). The invention is meant to include any other metrics for the degree of similarity or difference among Doppler spectra obtained over a range of depths. For example, measures related to coherence or correlation of Doppler spectra (either in the complex, magnitude or power domain) can be used to differentiate between signal, noise, and interference, therefore are fully contemplated for carrying out the invention.

Exemplary Similarity Metric: Statistical Coefficient of Variation:

1. Noise

Calculation of Doppler spectra from radio frequency (RF) ultrasound signals typically involves application of demodulation, range gating, clutter or wall-motion filtering, and a Fourier transform. These steps represent linear processing steps, such that the statistics of the real and imaginary components of the Doppler spectra can be described by a Gaussian distribution as long as the RF input signal such as noise is also Gaussian, which is typically the case for (background) noise signals.

In the next computational step towards magnitude or power spectra, the distribution of signals changes:

In case of magnitude spectra, signals with a Gaussian distribution are transformed into signals with a Rayleigh distribution with probability density function $$f(x; \theta) = \frac{x}{\theta^2} e^{-\frac{x}{(2\theta)^2}}$$

This distribution has mean value $$\mu = \theta\sqrt{\frac{\pi}{2}}$$

and standard deviation $$\sigma = \theta\sqrt{\frac{4-\pi}{2}}.$$

The scale parameter $\theta$ (often denoted as $\sigma$, but here as $\theta$ to avoid confusion with the standard deviation) refers to the standard deviation of the initial Gaussian distribution prior to magnitude spectrum estimation.

In case of power spectra, signals with a Gaussian distribution are transformed into signals with an exponential distribution with probability density function $$f(x; \lambda) = \lambda e^{-\lambda x}$$

This distribution has mean value $$\mu = \frac{1}{\lambda}$$

and the standard deviation $$\sigma = \frac{1}{\lambda}.$$

The parameter $\lambda$ is the rate parameter, which relates to the $\theta$ parameter of the Rayleigh distribution as $$\theta \sim \frac{1}{\sqrt{2\lambda}}$$

These statistical properties and relations between Gaussian, Rayleigh, and exponential distributions are known. Importantly for this invention, in either case the ratio between the standard deviation and the mean, also known as the coefficient of variation $$c_v = \frac{\sigma}{\mu}$$

or relative standard deviation, is constant:

in case of magnitude spectra (Rayleigh distribution) we have $$c_v = \sqrt{\frac{4-\pi}{\pi}} \approx 0.523;$$

in case of power spectra (exponential distribution) we have $c_v = 1$.

Either way, the coefficient of variation of the background noise in Doppler spectra is expected to be constant (e.g. independent of signal-to-noise ratio). For other metrics of similarity, we would expect a constant level in similarity of the noise in Doppler spectra.

2. Flow Signal

It is more difficult to find exact relations for the desired flow signal statistics. Being the result of backscattering by moving particles in the blood, the flow signal is, like noise, stochastic in nature. In a primary embodiment, we focus on the effects observed in the flow signal as a function of measurement depth. If multiple Doppler spectra are estimated at different depths with respect to the transducer, such as in WO2021/148416 A1, the statistics of the Doppler signal may be assessed. Apart from the stochastic variations, we typically see systematic differences in the Doppler spectrum intensity as a function of depth: at higher depths the flow signal becomes weaker because the larger distance the signal has to travel (resulting from both attenuation and spreading of the acoustic beam). This is shown in FIG. 3, which shows the Doppler spectra expressed in dB on a gray scale. In the image we can also appreciate the stochastic variation in the noise and the interference. The extent to which the flow signal intensity varies with depth depends on the measurement environment (e.g. size of the blood vessel, alignment of the acoustic beam with respect to the vessel, etc.). In general, though, the average flow signal intensity is higher than that of the noise, but its variation relative to average, i.e. the coefficient of variation, is even larger as a result of the systematic reduction in flow signal energy with depth. As a result, the similarity in flow signal intensities over depth is relatively low and the coefficient of variation relatively high as compared to noise.

3. Interference

In contrast to the flow and noise components, interference tends to be largely deterministic. Since the interference source is independent from the flow measurement system itself, there is no reason for the interference to vary with factors that relate to the Doppler ultrasound acquisition. For example, the depth we referred to earlier, in fact derives from the time since the last pulse transmission (via time of flight). As such, there is no systematic variation in interference components with depth (i.e., time on microsecond scale) or time (i.e. along the horizontal direction within one depth segment image, on a millisecond scale). In general, we typically observe interference as signal components with a relatively high mean intensity (above the noise level) but a low variation in intensity, such that there is a high degree of similarity in the Doppler spectrum intensity of interference over depth. Thus, the coefficient of variation for interference signals is expected to be smaller or lower than the coefficient of variation of the noise.

In summary, we have three distinct components that contribute to the Doppler spectrum whose statistical characteristics with respect to depth (but also time or frequency) are fundamentally different:

for the noise component (assuming Gaussian noise), the coefficient of variation is fixed by the laws of statistics. As noise is omnipresent, the mean of the noise level is lower than that of the other components;

for the signal component, the coefficient of variation is above that of the noise.

for the interference component, the coefficient of variation is below that of the noise.

When applying this analysis after logarithmic compression on the Doppler spectra (either magnitude or power), such that the spectral intensities are e.g. in a dB scale, the multiplicative nature of the noise becomes additive instead. In this domain, one should therefore not consider the relative standard deviation or coefficient of variation, but rather the absolute standard deviation (e.g. in dB).

Algorithm for Detection and Suppression of Interference

A high-level algorithm for detection and suppression of interferences can now be described based on Doppler spectrum data in three dimensions:

time t, describing the time points at which successive Doppler spectra are evaluated;

frequency f, describing the frequency points over which the Doppler spectrum is evaluated. Frequency is proportional to the flow velocity and can be used interchangeably;

depth d, describing the depth points at which successive Doppler spectra are evaluated.

The algorithm comprises the following steps, that operate locally on (time t, frequency f) point in the spectrum data:

1. estimate local similarity metrics from the Doppler spectrum data as function of d (and possibly t and f);
2. from the estimated statistical properties, instantaneously infer whether a data point in the Doppler spectrum is affected by interference;
3. optionally, track the history of the similarity metrics over time for adaptive learning and tracking of interference components over time for a more robust detection;
4. if interference is detected, apply a correction or suppression with the aim of removing the interference component from said data point. Correction can be done for specific purposes, such as
   a. improvement of visual perception of the Doppler image;
   b. improvement of the Doppler audio signal quality;
   c. improvement of the robustness with which the spectra can be postprocessed (e.g. estimation of IPV, APV, and derived clinical diagnostic parameters such as coronary flow reserve (CFR)).

Exemplary Embodiments for these Steps are Detailed Below

1. Statistical properties over depth (e.g. mean u, standard deviation $\sigma$, $c_v$, and potentially higher order statistics) can be estimated locally within a kernel (i.e. local region spanning time, frequency and depth) that shifts across the time and frequency axes. Filtering (e.g. smoothing or median filtering) may be applied over time and frequency on the spectrum data before estimation, and/or on the resulting maps of the statistical properties to improve the robustness of the estimation.
2. Different features can be used to instantaneously assess whether a data point is affected by interference. These features may also be filtered (e.g. low-pass filtered) over frequency and time.
   a. in an embodiment, the observed local coefficient of variation is used as a feature. A (soft) threshold can be set, e.g. at a level slightly below the expected coefficient of variation for noise in order to differentiate between interference on the one hand and either signal or noise on the other hand;
   b. in another embodiment, a prediction is made for the average of the local spectrum data $\hat{\mu}$ based on the observed standard deviation $\hat{\sigma}$ and the constant noise coefficient of variation $c_{v,n}$ as $$\hat{\mu} = \frac{\hat{\sigma}}{c_{v,n}}$$

If this prediction is below the observed average of the local spectrum data, the amount of variation observed is too low in comparison to the average. This is a sign that the data point is affected by interference;
   c. in another embodiment, the coherence or any other measure of similarity among spectrum data points over depth is used as feature to differentiate between interference on the one hand and either signal or noise on the other hand;

d. in conjunction with any of the preceding features, the instantaneous average of the Doppler spectrum can be used to assess whether a data points represents the noise class (and this does not need to be considered as potential interference) by checking if the instantaneous average of the Doppler spectrum over depth is significantly above the global noise level.

3. In particular, since interference often manifests itself in the form of horizontal lines that are slowly varying with time, the history of a particular frequency point (or in general neighboring data points including non-causal, future data points) in the Doppler spectrum can be a relevant indicator. This can for example be considered in a Bayesian or other probabilistic framework (in particular, Markov models could be used to map the probability of a data point to represent different classes such as signal, noise, and interference). A prior probability, describing the chance for a data point to be affected by interference without having seen its spectral intensity, can be constructed based on the history over the observed similarity over time (and/or frequency) using any of the approaches listed. This a priori probability may be learned over time. The likelihood that the current data point is affected by interference can be derived from the instantaneous similarity feature using any of the approaches listed. In Bayesian sense, the final probability of a datapoint being affected by interference is then related to the product of the a priori probability and the likelihood.

4. Correction of interference-affected data points in the Doppler spectrum can be done in several different ways:
   a. one strategy is to effectively replace the Doppler spectrum intensity in interference by the intensity of the noise:
      i. in a basic form, interference-affected data points in the Doppler spectrum are corrected to a level corresponding to the overall noise floor;
      ii. alternatively, a soft correction method, e.g. using a sigmoid function, can be used to mix the original data point with the noise level. This would reduce the amount of correction done in data points in which it is less certain that interference components are present (or to a lesser extent). The soft correction can be combined with any of the detection approaches to have a soft thresholding and correction approach;
   b. in another strategy, instead of replacing interference by noise, the goal is to subtract the interference contribution from the signal. In principle this approach has the benefit that desired flow signal contents can be preserved. Estimation of the interference component $\tilde{a}$ is possible as the difference between the observation $\tilde{\mu}$ and the prediction $\hat{\mu}$ for the average of the local spectrum as outlined above:

$$\tilde{\alpha} = \tilde{\mu} - \hat{\mu} = \tilde{\mu} - \frac{\tilde{\sigma}}{c_{v,n}}$$

c. in a third alternative, data points (pixels) affected by interference are replaced by image interpolation, e.g. by the average of surrounding pixels that are not affected by interference;

d. another alternative involves estimation and display of Doppler images directly from standard deviation, variance or similarity feature instead of from the average;
   e. another alternative is to combine methods, e.g. apply the suppression of method c. and subsequently apply smoothing;
   f. correction can also be implemented as an adaptive process, where a measure derived from the similarity feature can be used as a step-size parameter to control the update rate of (frequency dependent) adaptive filters to remove correlated interference components. This method automatically takes history about presence of correlated interference into account in the learned filter parameters and allows for cancellation of interference in regions where also signal is present.

Demonstration of Primary Embodiment

In an embodiment, suppression of interference components is implemented by the following steps:
   1. Doppler spectra are obtained using the following acquisition scheme and parameters:
      a. 32-cycle ultrasound burst at 12.5 MHz and a pulse repetition frequency of 71 kHz;
      b. quadrature demodulation of radiofrequency (RF) data at 50 MHz sampling rate to in-phase and quadrature (IQ) data at 25 MHz sampling rate;
      c. packet filtering of each RF line with a moving average over 32 cycles and downsampling of IQ data to packets. Each packet represents a 2-mm depth range; 7 packets are obtained for over a start depth range from 3-9 mm, respectively, with a 1-mm sampling distance between subsequent packets;
      d. wall-motion filtering with a recursive high pass filter applied to the packet filtered data;
      e. at each depth, the Doppler spectrum is estimated by a Fourier transform of the IQ packet data at each depth over 512 successive pulse-echo acquisitions. A Hamming window is used and an overlap of 50%, i.e., 256 acquisitions, is implemented between successive Doppler spectrum evaluations over time. Along the frequency axis, 1024 samples are obtained (69 Hz/sample), along the time axis a spectrum is obtained every 3.6 ms;
      f. magnitude Doppler spectra are obtained by taking the absolute value of the complex frequency-domain Doppler spectrum data, which are thus available in three dimensions being time t, frequency f, and depth d;
   2. at each (t, f) coordinate, the mean $\tilde{\mu}(t, f)$ and standard deviation $\tilde{\sigma}(t, f)$ of the magnitude are estimated over depth;
   3. the mean and standard deviation are smoothed using a 3×3 moving average, resulting in smoothed $\tilde{\mu}_s(t, f)$ and $\tilde{\sigma}_s(t, f)$;
   4. at each data point (t, f), interference is detected if $$\tilde{\sigma}_S(t, f) < k \cdot (c_{v,n} \cdot \tilde{\mu}_S(t, f) - \Delta\sigma)$$

Here k and $\Delta\sigma$ are parameters that define the classification threshold. The factor k defines how the classification threshold scales with the expected coefficient of variation and a suitable value would be just below 1, e.g. 0.9 to allow for some margin with respect to the expect. Similarly, $\Delta\sigma$ defines an offset by which the standard deviation may deviate from its expectation. A suitable value for $\Delta\sigma$ is e.g. 0.15 (after ensuring the spectrum data are normalized such that the mean noise level equals 1);

5. at data points (t, f) where interference is detected, the interference component $\tilde{a}$ is calculated from the unsmoothed mean and standard deviation as $$\tilde{\alpha} = \max\left\{0; \tilde{\mu}(t, f) - \frac{\tilde{\sigma}(t, f)}{c_{v,n}}\right\}$$

This term is lower bounded by 0; it is subtracted from the observed average magnitude spectrum so the corrected mean $\mu_c$ (t, f) becomes $$\mu_c(t, f) = \tilde{\mu}(t, f) - \tilde{\alpha} = \min\left\{\tilde{\mu}(t, f); \frac{\tilde{\sigma}(t, f)}{c_{v,n}}\right\}$$

For an example dataset, the described algorithm is visualized below. A segment of a Doppler spectrum is shown in FIG. 4. In this image, three regions of interest (ROIs) are defined to represent noise, the desired flow signal, and interference, respectively. It should be noted that the interference ROI also contains some pixels featuring only noise; and the flow signal ROI likely contains some interference components near 0.1 m/s (though they are overshadowed by the desired signal).

In FIG. 5 the average of the magnitude spectrum over depth is plotted against the standard deviation of the magnitude spectrum over depth for all pixels within the ROIs of FIG. 4. Generally speaking we can see some trends:

both the average and standard deviation of the noise pixels are relatively low. Generally, the values are reasonably in line with the expected relation between mean and standard deviation, although per-pixel variations are substantial;

for the interference pixels, the mean is spread over a relatively wide range, whereas the standard deviation is in fact rather close to that of the noise pixels. Although again the points are spread, for the majority of interference pixels the coefficient of variation is below the expected coefficient of variation of the noise;

the signal pixels reveal a very broad distribution in both mean and standard deviation, representing the wide range of signal amplitudes that can be observed. Generally, the majority of signal pixels have a coefficient of variation above the coefficient of variation of the noise, but the distribution is broad enough that there are many pixels whose coefficient of variation is similar or even below the coefficient of variation of the noise. In this example, all pixels in the signal ROI show a larger average than the noise level, however this may not always be the case. In such transition areas between signal and noise, lower mean values are expected but still the coefficient of variation is expected to be at least the statistical coefficient of variation of the noise.

To reduce the spread of the distributions for the observed mean and standard deviation, prior information is taken into account. In this example a moving average over 3 by 3 pixels is applied on the mean and standard deviation to reduce the spread. This is shown in FIG. 6, which reveals that the general trends are retained while concentrating the observed distributions for mean and standard deviation more closely around their average. This allows better separation of the different classes, and thus a better classification of interference-affected pixels. In this figure, the adopted classification threshold is shown as a dotted line; all pixels whose observed standard deviation is below the dotted line are deemed to be affected by interference.

A correction is applied to the interference-affected pixels; the correction is applied on the pixels statistics prior to smoothing, i.e. those shown in FIG. 5. The corrected mean versus the original standard deviation is shown in FIG. 7. For pixels not classified as interference, the data points are identical to those in FIG. 5; pixels that are classified as interference generally have their mean value shifted to the left to bring it in line with the expected relation between mean and standard deviation for noise. This approach essentially subtracts the estimated interference contribution or energy from the average magnitude spectrum value.

The overall result of the correction algorithm is shown in FIG. 8. If we compare this to the original data in FIG. 4, we see that the interference components are effectively reduced while other parts of the image are largely unaffected.

Various Examples of the present disclosure and in which the techniques disclosed above are implemented, are detailed below.

Example 1. An apparatus for flow measurement in a vessel, comprising a processor configured to:

obtain a plurality of ultrasound signals from an ultrasound transducer of an interventional device, wherein the plurality of ultrasound signals originate from a range of depths within the vessel with respect to the ultrasound transducer;

ascertain from the plurality of ultrasound signals, flow velocity spectra over the range of depths;

detect a measure for similarity or variation of the flow velocity spectra over the range of depths; and obtain a composite flow velocity spectrum over the range of depths within the vessel by suppressing interference components from the flow velocity spectra based on the measure for similarity or variation of the flow velocity spectra over the range of depths.

In Example 1, the interventional device may be a guidewire, a FloWire, a ComboWire, a pressure wire, or the Doppler wire illustrated in FIG. 1, for example. In standard ultrasound pulsed Doppler measurements, the blood velocity in a specific sampling area is deduced by analysing the ultrasound signals that originate from a specific depth within the blood vessel, such as from the depth marked by the dark band labelled Sample Volume in FIG. 1. By contrast, in Example 1, the plurality of ultrasound signals that are obtained originate from a range of depths within the vessel with respect to the ultrasound transducer. With continued reference to FIG. 1, an example of the range of depths within the vessel with respect to the ultrasound transducer, is the range of distances from the Transducer that are encompassed by the line marked 28° and the right-hand side of the dark band labelled Sample Volume in FIG. 1.

In Example 1, the operation of ascertaining flow velocity spectra over the range of depths may be performed as described above, e.g. using pulsed-wave Doppler processing.

In Example 1, the operations of detecting a measure for similarity or variation may be performed as described above, and also as described in the Examples below.

Example 2. The apparatus of Example 1, further comprising a display, or an audio device, and wherein the processor is configured to output to the display the composite flow velocity spectrum over the range of depths, or a parameter derived from it;

or
wherein the processor is configured to output to the audio device an audio signal representing the composite flow velocity spectrum over the range of depths.

In Example 2, an example of the display to which the composite flow velocity spectrum over the range of depths is outputted, is the display 6 illustrated in FIG. 9. In Example 2, the audio device may for example be a loudspeaker, headphones, and so forth.

Example 3. The apparatus of Example 2, wherein the processor is further configured to:
identify as flow signal components, portions of the flow velocity spectra having a relatively lower value of the measure for similarity over the range of depths; and
identify as the interference components, portions of the flow velocity spectra having a relatively higher value of the measure for similarity over the range of depths;
or:
identify as flow signal components, portions of the flow velocity spectra having a relatively higher value of the measure for variation over the range of depths; and
identify as the interference components, portions of the flow velocity spectra having a relatively lower value of the measure for variation over the range of depths.

In Example 3, the flow signal components and the interference components may be identified using various techniques. For example, the flow velocity spectra may be outputted to a display device, and the relevant portions identified by highlighting, or colouring, or shading, or labelling, and so forth.

Example 3a. The apparatus of Example 3, wherein the processor is further configured to identify as noise components, portions of the flow velocity spectra having a magnitude that is below a predetermined value.

In Example 3a, the predetermined value that is used to identify the noise components may be determined empirically. For example the predetermined value may be determined by sampling the Doppler spectrum in a region of high velocity in which it is not expected that there will be any flow signal components. In this region, the statistics of the flow velocity spectra may then be determined using the approach described with reference to FIG. 5, wherein the theoretical value the expected coefficient of variance for noise, $c_{v,n}$, is used to assess whether the sampled region of the Doppler spectrum is contaminated by interference. If plotted as illustrated in the graph in FIG. 5, the noise would be expected to appear as a distribution of points on a diagonal line that coincides with the line labelled Expected $c_{v,n}$ (noise). Thus, by plotting a graph as illustrated in FIG. 5, a threshold value, i.e. the predetermined value of the magnitude of the flow velocity spectrum, may be set which separates noise, which lies on the diagonal line labelled Expected $c_{v,n}$ (noise), from flow signal components, or interference components. After the predetermined value has been obtained, the predetermined value may be stored in a lookup table, or a memory, and recalled for use in the apparatus without the need to repeat the sampling procedure.

Example 4. The apparatus of any one of Examples 1-3, wherein the processor is configured to detect the measure for similarity or variation of the flow velocity spectra over the range of depths by performing a statistical analysis on the flow velocity spectra, or by calculating a value of a correlation metric for the flow velocity spectra, or by calculating a value of a coherence metric for the flow velocity spectra.

Example 5. The apparatus of Example 4, wherein the processor is configured to detect the measure for variation of the flow velocity spectra over the range of depths by performing a statistical analysis on the flow velocity spectra, and wherein the performing a statistical analysis on the flow velocity spectra comprises:
calculating mean and/or standard deviation and/or variance values for the flow velocity spectra over the range of depths to provide the measure for the variation of the flow velocity spectra over the range of depths.

Example 6. The apparatus of Example 5, wherein the performing a statistical analysis on the flow velocity spectra comprises calculating mean and standard deviation values for the flow velocity spectra over the range of depths; and
wherein the processor is configured to:
identify as flow signal components, portions of the flow velocity spectra having relatively higher values of the measure for the variation of the flow velocity spectra over the range of depths; and
identify as the interference components, portions of the flow velocity spectra having relatively lower values of the measure for the variation of the flow velocity spectra over the range of depths; and
wherein the measure for the variation of the flow velocity spectra over the range of depths is provided by the standard deviation values, or by a ratio ($c_v$) of the standard deviation values to the corresponding mean values; and
wherein the relatively higher values of the measure for the variation of the flow velocity spectra over the range of depths, and the relatively lower values of the measure for the variation of the flow velocity spectra over the range of depths are evaluated with respect to a classification threshold.

The operations performed in Example 6 are described above with reference to FIG. 5-FIG. 8.

Example 7. The apparatus of Example 6, wherein the classification threshold is calculated based on a ratio ($c_{v,n}$) of a standard deviation (o) to a mean value (u) for an expected noise spectrum.

Example 7a. The apparatus of Example 7, wherein the classification threshold comprises an error margin, and wherein the error margin reduces a value of the classification threshold.

An example of the error margin is the Classification threshold described above with reference to FIG. 6.

Example 8. The apparatus of Example 6 or Example 7, wherein the measure for the variation of the flow velocity spectra over the range of depths is provided by the ratio ($c_v$) of the standard deviation values to the corresponding mean values; and
wherein the processor is configured to:
identify as the flow signal components, the portions of the flow velocity spectra having relatively higher values of the ratio ($c_v$) of the standard deviation value to the mean value; and
identify as the interference components, the portions of the flow velocity spectra having relatively lower values of the ratio ($c_v$) of the standard deviation value to the mean value.

Example 9. The apparatus of Example 6, wherein the measure for the variation of the flow velocity spectra over the range of depths is provided by the standard deviation values; and
wherein the processor is further configured to:
identify as flow signal components, portions of the flow velocity spectra having a relatively lower value of the standard deviation at the corresponding mean value; and identify as the interference components, portions of the flow velocity spectra having a relatively higher value of the standard deviation at the corresponding mean value; and wherein the relatively higher value of the standard deviation, and the relatively lower value of the standard deviation, are evaluated at the corresponding mean value with respect to a classification threshold; and wherein the classification threshold is calculated based on a ratio ($c_{vn}$) of the standard deviation ($\sigma$) to the mean value ($\mu$) for an expected noise spectrum, and the corresponding mean value.

Example 10. The apparatus of Example 9, wherein the classification threshold comprises an error margin, and wherein the error margin reduces a value of the classification threshold, and wherein the error margin is calculated based on: the ratio ($c_{vn}$) of the standard deviation ($\sigma$) to the mean value ($\mu$) for the expected noise spectrum, and the corresponding mean value ($\tilde{\mu}_s$ (t, f), and an offset value $\Delta\sigma$ for the standard deviation and/or a gradient multiplication factor, k; and wherein the classification threshold $\tilde{\sigma}_{Th}$ (t, f) comprising the error margin is calculated for the portion of the flow velocity spectra at a time, t, and a frequency, f, using the equation:

$$\tilde{\sigma}_{Th}(t, f) = k \cdot (c_{vn} \cdot \tilde{\mu}_S(t, f) - \Delta\sigma)$$

wherein ($\tilde{\mu}_s$ (t, f) represents the corresponding mean value of the spectrum at the time, t, and the frequency, f.

Example 10a. The apparatus of Example 6, wherein the processor is further configured to:

identify as noise components, portions of the flow velocity spectra having mean values that are below a predetermined value.

Example 11. The apparatus of any previous Example, wherein the suppressing interference components from the flow velocity spectra based on the measure for similarity or variation, comprises:

replacing the interference components in the flow velocity spectra with expected corresponding noise components; or subtracting the interference components from the flow velocity spectra; or wherein the apparatus further comprises a display, and wherein the processor is further configured to output to the display the composite flow velocity spectrum as an image comprising a plurality of pixels, and wherein pixels in the displayed image have intensity values that are determined by replacing pixels in the flow velocity spectra that represent interference components with interpolated values that are calculated from neighbouring positions in time and frequency in the composite flow velocity spectrum that do not represent interference components.

In Example 11, with reference to FIG. 5, the operation of subtracting the interference components from the flow velocity spectra may be performed for an individual pixel by calculating the expected mean value of the pixel from the measured standard deviation, using the value of $c_{v,n}$ for noise using the equation above under section 1. Noise, and subtracting the difference between the measured mean value and the expected mean value, from the measured mean value.

Example 12. The apparatus of any previous Example, wherein:

the ascertaining flow velocity spectra further comprises filtering the plurality of ultrasound signals in the time domain or in the frequency domain; and/or wherein the processor is configured to detect the measure for similarity or variation of the flow velocity spectra by performing a statistical analysis on the flow velocity spectra; and wherein the processor is further configured to smooth the values obtained from the statistical analysis prior to detecting the measure for similarity or variation of the flow velocity spectra.

Example 13. The apparatus according to any previous Example, further comprising a display, and wherein the processor is configured to:

estimate, from the composite flow velocity spectrum, a value of one or more of: an instantaneous peak velocity, IPV, an average peak velocity, APV, and a coronary flow reserve, CFR; and output, to the display, the respective value(s).

In Example 13, the value(s) for the IPV, the APV, and the CFR, may alternatively be outputted as audio messages.

Example 14. An apparatus for flow measurement in a vessel, the apparatus comprising a processor configured to:

obtain a plurality of ultrasound signals from an ultrasound transducer of an interventional device, wherein the plurality of ultrasound signals originate from a range of depths within the vessel with respect to the ultrasound transducer;

ascertain from the plurality of ultrasound signals, flow velocity spectra over the range of depths;

detect a measure for similarity or variation of the flow velocity spectra over the range of depths; and identify one or more interference components from the flow velocity spectra based on the measure for similarity or variation of the flow velocity spectra over the range of depths.

In Example 14, the one or more interference components may be identified using various techniques, such as by highlighting, or colouring, or shading, or labelling, the interference component(s) and so forth.

Example 14a. The apparatus of Example 14, further comprising a display, and wherein the processor is configured to output to the display, a graphical representation of the flow velocity spectra over the range of depths including an identification of the one or more interference components.

In Example 14a, an example of the display to which the graphical representation of the flow velocity spectra is outputted, is the display 6 illustrated in FIG. 9.

Example 14b. The apparatus of any previous Example, wherein the processor is configured to detect the measure for similarity or variation of the flow velocity spectra over the range of depths and/or to obtain the composite flow velocity spectrum over the range of depths within the vessel and/or to identify the one or more interference components from the flow velocity spectra, by inputting the ascertained flow velocity spectra over the range of depths, into a neural network; and wherein the neural network is trained to detect the measure for similarity or variation of the flow velocity spectra over the range of depths and/or to obtain the composite flow velocity spectrum over the range of depths within the vessel and/or to identify the one or more interference components from the flow velocity spectra, respectively.

In Example 14b, the use of various architectures for the neural network is contemplated. For instance, the neural network may have a convolutional neural network, "CNN" architecture, an encoder-decoder architecture, a recurrent neural network "RNN" architecture, a transformer architecture, and so forth. In Example 14b, the ascertained flow velocity spectra over the range of depths may be ascertained from a plurality of ultrasound signals from an ultrasound transducer of an interventional device, as described above, and wherein the plurality of ultrasound signals originate from a range of depths within the vessel with respect to the ultrasound transducer. In this regard, the ultrasound signals may represent a packet length that exceeds an ultrasound pulse length.

Example 15. The apparatus of any previous Example, wherein the plurality of ultrasound signals represent backscattered ultrasound radiation originating from moving particles in blood in the vessel at the plurality of depths, the backscattered ultrasound radiation being backscattered in response to ultrasound radiation emitted by the ultrasound transducer.

II. SYSTEM AND METHOD FOR INTERFERENCE-FREE DRIVING OF ELECTRONICS FOR INTRAVASCULAR DOPPLER FLOW MEASUREMENTS

The intravascular flow measurement is potentially susceptible to further interference signals. An example is in fact shown in FIG. 2, where we can see a clear example of interference that manifests itself as the bright white horizontal line near the top of the Doppler spectrum image, just above 90 cm/s. Had this line been positioned somewhat lower and partially overlaid with the flow signal component, this line would have complicated the IPV estimation and potentially caused erroneous measurements. Interference may be caused by external sources, by the flow measurement system electronics itself or by both.

According to an aspect of the invention the focus is on internally caused interferences, that can be caused for example by switching electronics. Such electronics, e.g. used for DC voltage supply, are both energy-efficient and cost-effective and therefore attractive in any electronics implementation. Their downside is that they produce harmonic distortion that may couple in to the receive signal path for flow, causing interferences in the Doppler spectrum akin to those in FIG. 2.

The object of the invention involves a specific operation mode of the flow system electronics that prevents the harmonic distortion of switch-mode electronics from affecting the flow measurement. The electronics are driven at a fixed pattern that is repetitive with a frequency that is exactly an integer multiple of the ultrasound pulse repetition frequency (PRF). This causes all the harmonic frequencies of the electronics to also be harmonics of the PRF. As such, all distortion is forced to the 0 cm/s velocity component in the Doppler flow velocity image, which is suppressed from the Doppler image by clutter filtering that is routinely used in any Doppler application (the clutter filter causes the black horizontal band in the Doppler image of FIG. 2 around the 0 cm/s velocity).

Detailed Description of how to Build and Use the Invention

An implementation corresponding to an example embodiment is shown in FIG. 9. This shows the situation in which two distinct switch-mode power supplies are controlled in such a way that they are synchronized with respect to the ultrasound data acquisition of the flow velocity signal. This is realized by ensuring that the binary switch signal for each of the power supplies repeats itself at a period that corresponds exactly to the pulse repetition interval (PRI, denoted as $t_{period}$ in FIG. 9).

In this example, the switch-mode frequency exceeds the PRF. It is not strictly necessary for the switch signals to be periodic within the PRI. The pattern must however be repetitive with the PRI.

As the PRF is a variable within the system, the used frequency for the switch-mode electronics is also variable. The number of periods for each switch-mode module is calculated by software to get as close as possible to the desired switch mode frequency, without violating the fixed number of periods within a PRI. For example, the switch mode frequency could be chosen as the integer multiple of the PRF that is closest to the desired switch mode frequency.

In practice, due to the finite clock resolution in any implementation, it may not be possible to exactly realize the desired switch-mode frequency. In such cases we can exploit the fact that the switch-mode does not require a perfectly periodic switch signal that can tolerate jitter to some extent. This is highlighted by the following numerical example:

center frequency: 12.5 MHz;

digital clock frequency: 100 MHz, so the time resolution for the switch-mode driving signal is 10 ns;

PRI: 176 periods @ 12.5 MHz so:
  PRF=71.0 kHz;
  PRI=1408 clock periods;

target switch-mode frequency: 400 kHz;

adopted switch-mode frequency closest to the target:
  6*PRF=426 kHz;
  switch-mode period=2.3467 us or 234.67 clock periods that alternate between low and high;
  low: 117.33 clock periods;
  high: 117.33 clock periods;

example scheme for switch signal over 1408 clock periods that repeats itself synchronously with the ultrasound transmission:
  1. 117 clock periods high;
  2. 117 clock periods low;
  3. 118 clock periods high;
  4. 117 clock periods low;
  5. 117 clock periods high;
  6. 118 clock periods low;
  7. 117 clock periods high;
  8. 117 clock periods low;
  9. 118 clock periods high;
  10. 117 clock periods low;
  11. 117 clock periods high;
  12. 118 clock periods low.

The implementation of the aspect disclosed in section II may be combined with any of the examples of the aspect disclosed in section I.

Alternatively, the aspect disclosed in section II may be implemented standalone, with following non-extensive examples:

i) an apparatus for flow measurement in a vessel, comprising:
  at least one switch-mode power supply; and
  at least one processor configured to control the at least one power supply and to control the ultrasound data acquisition of the flow velocity signal in such a way that the operation of the at least one power supply is synchronized with respect to the ultrasound data acquisition of the flow velocity signal;

ii) the apparatus of i) wherein a binary switch signal is provided for the at least one power supply, which binary switch signal repeats itself at a period that corresponds exactly with the pulse repetition interval of the ultrasound data acquisition of the flow velocity signal.

III. GENERAL CONSIDERATIONS ON THE SYSTEMS AND METHODS ACCORDING TO ANY OF THE EMBODIMENTS OF THE DISCLOSED INVENTIONS

The exemplary system is illustrated in FIG. 10. The interventional device 1 such as the intravascular device (e.g. FloWire, ComboWire or pressure wire) is connected by wired or wireless connection to an apparatus 5, e.g. a console, or through a patient interface module to the console. The console may provide the electrical excitation pulse to the ultrasound transducer. Alternatively, the electrical excitation pulse could be provided by an autonomous electrical component that is integrated in the patient interface module. The proximal portion of the interventional device remains outside of the body of the patient 7 during flow measurement or pressure measurement with the distal portion of the interventional device inserted into the anatomical structure of the patient, e.g. blood vessel. In a further alternative the electrical source is integrated in the proximal portion of the interventional device and is configured to communicate with an application specific integrated circuit (ASIC) located nearby the ultrasound transducer in the distal portion of the interventional device, which ASIC provides then the electrical excitation pulses for the ultrasound transducer. Optionally, the measurement data can be transmitted wirelessly directly to a user interface such as a display 6. In any of the embodiments a processor is involved in processing the measurement data to output the result of the flow or pressure measurement. The processor may be integrated in at least one of: the console, the display and patient interface module. The measurement result may be presented on a user interface in the form of a visual representation (e.g. graphical and/or numerical), or it can be presented as acoustic signal, wherein the acoustic characteristics of the signal vary according to the output flow result.

The system 10, schematically illustrated in FIG. 10, may comprise in various alternative configurations the following components:

the interventional device wherein the processor is integrated within the proximal portion of the interventional device, further comprising a user interface for outputting the flow results, and wherein the processor communicates through wireless communication with the user interface;

the interventional device in wired or wireless communication with a console that comprises the processor, and which outputs the flow result to the user interface, which user interface can be separate from or integrated in the console.

In any of the embodiments, the system may further comprise at least an extracorporeal apparatus 8 suitable for providing at least one of the imaging modalities: x-ray angiography, computer tomography, ultrasound imaging and magnetic resonance imaging.

A computer program comprising code means may be provided, which when run on a computer or a processor, implements any of the methods according to any of the embodiment of the invention on any of the systems according to the invention. The computer program may be stored and/or distributed on a suitable medium, such as an optical storage medium or a solid-state medium, supplied together with or as part of other hardware, but may also be distributed in other forms, such as via the Internet or other wired or wireless telecommunication systems.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

Figure 1:
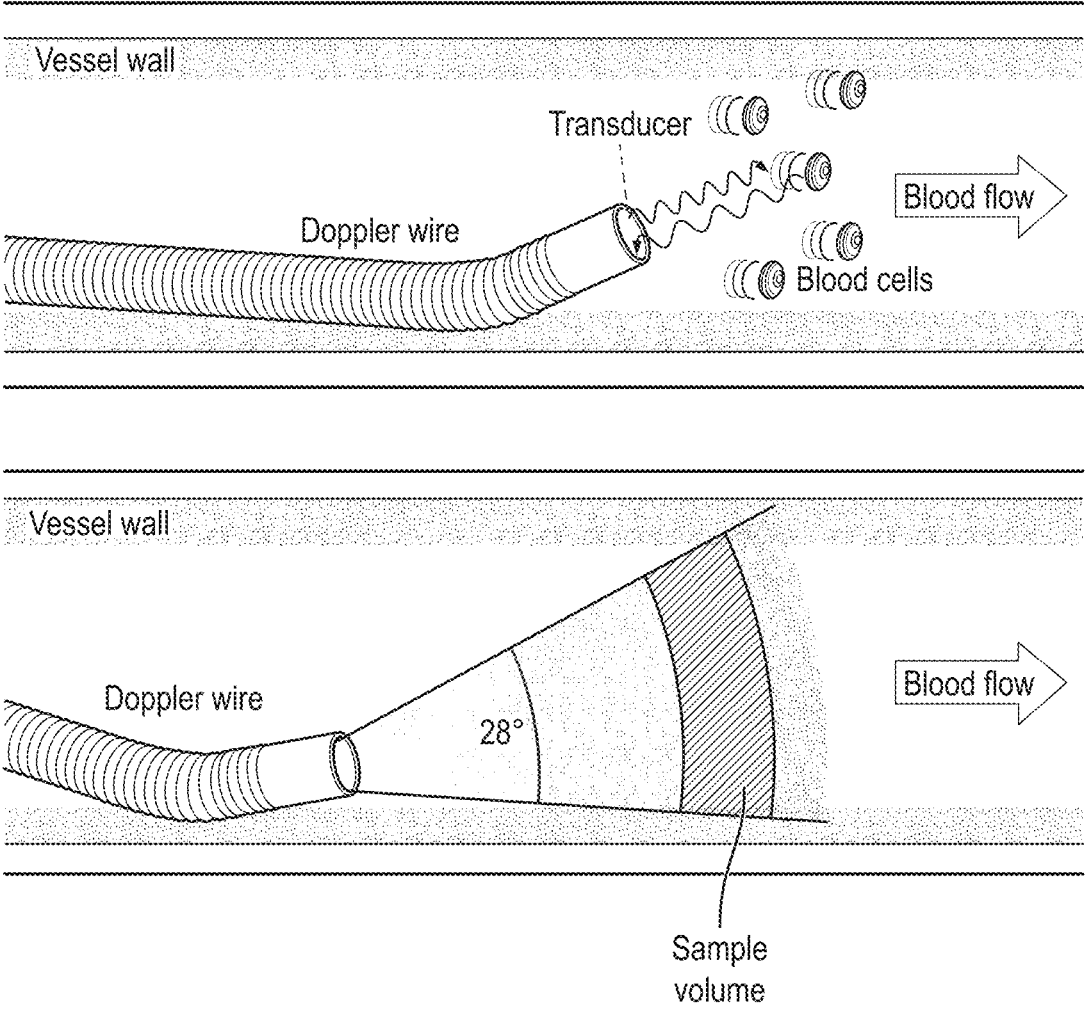
FIG. 1. Illustrative example of the FloWire inside a blood vessel. Top: The ultrasound waves transmitted and received by the PZT tip. Bottom: Example of the sample volume.
Figure 2:
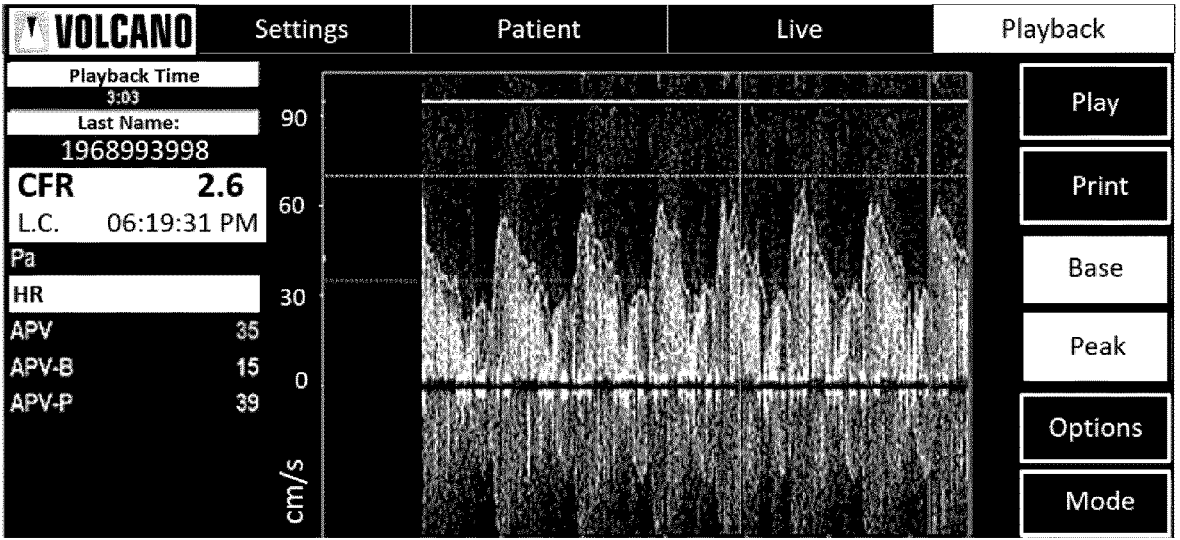
FIG. 2. Example of a velocity measurement. The blue contour (IPV) is the estimated peak velocity as function of time; the APV is numerically shown on the left-hand side and represents the average value of the blue contour over one or more consecutive cardiac cycles.
Figure 3:
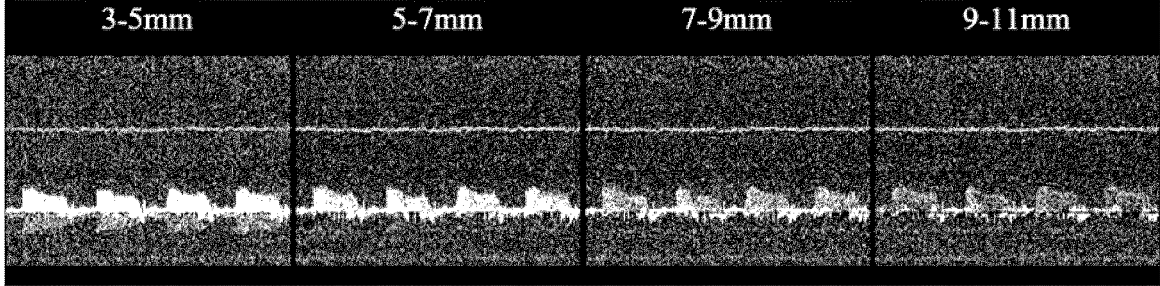
FIG. 3. Doppler spectra obtained at various depths. Four spectra are plotted as function of time (horizontal axis) and velocity (vertical axis) over the course of 4-5 heart beats.
Figure 4:
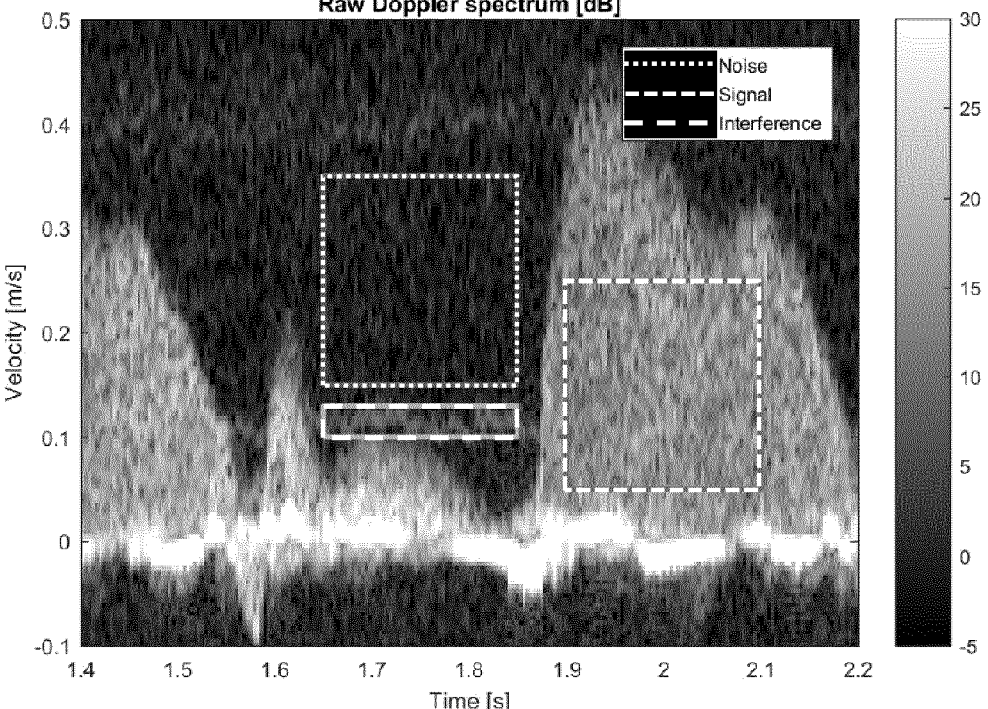
FIG. 4. Original Doppler spectrum obtained from within a coronary artery with selected ROIs representing noise (blue), signal (red) and interference (yellow). The spectrum is normalized such that the noise level is at 0 dB.
Figure 5:
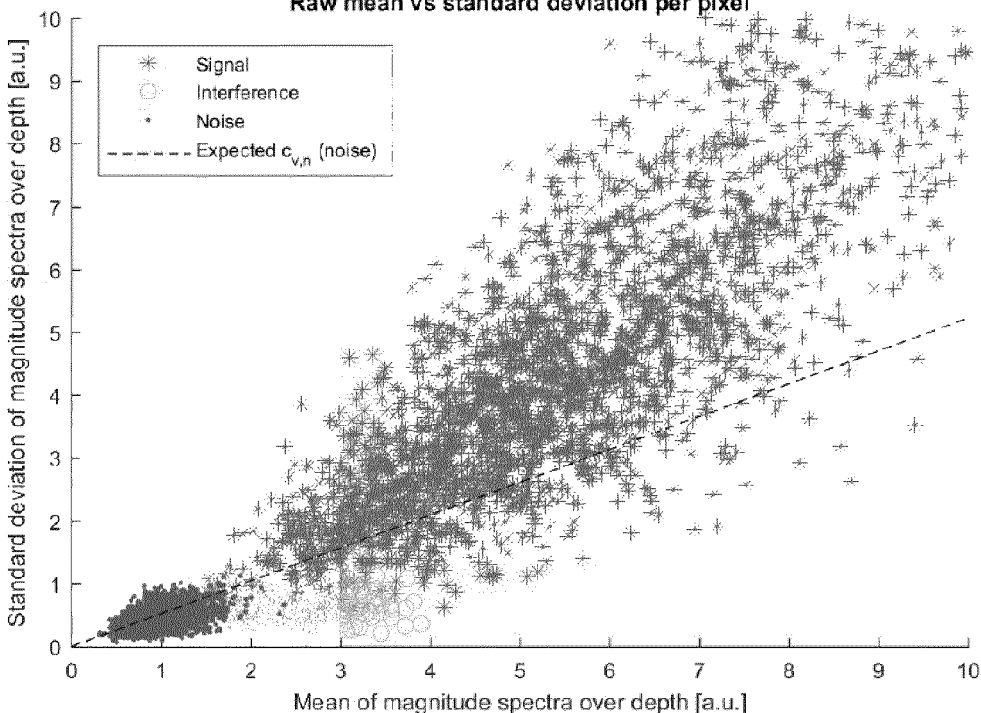
FIG. 5. Mean vs. standard deviation of the magnitude spectrum over depth of all pixels within the signal, interference, and noise ROIs as drawn in FIG. 4. Also shown is the expected relation between mean and standard deviation in case of noise.
Figure 6:
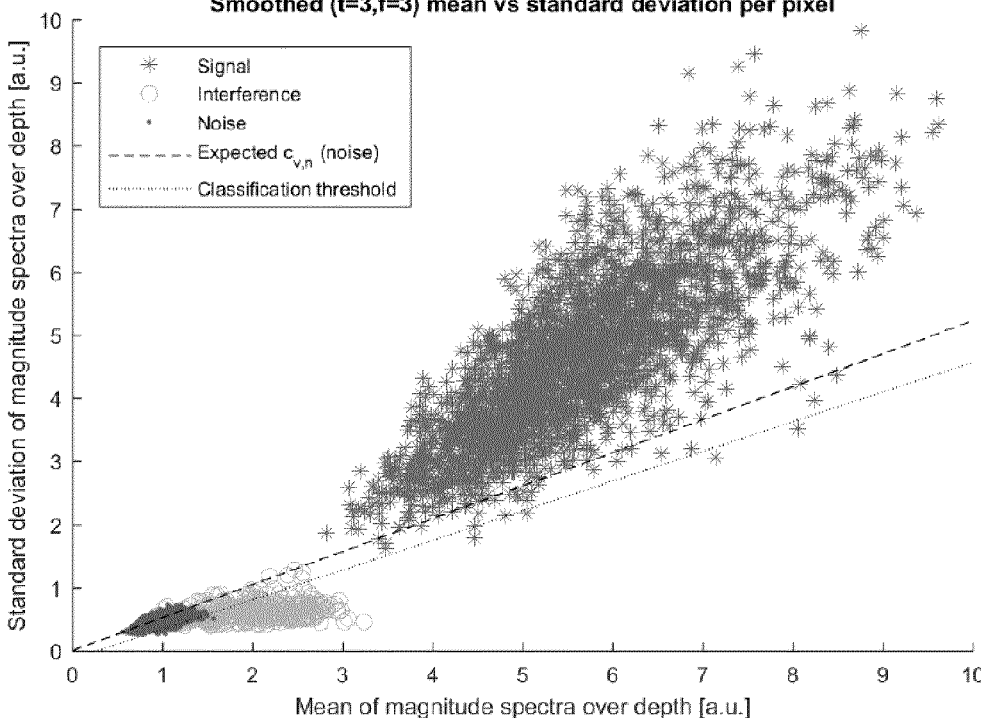
FIG. 6. Mean vs. standard deviation over depth of all pixels within the ROIs shown in FIG. 4 after application of smoothing on the mean and standard deviation values (moving average over 3×3 pixels). Also shown are the expected relation between mean and standard deviation in case of noise (dashed black line) and the adopted classification threshold (dotted black line). Data points below the classification threshold are classified as interference.
Figure 7:
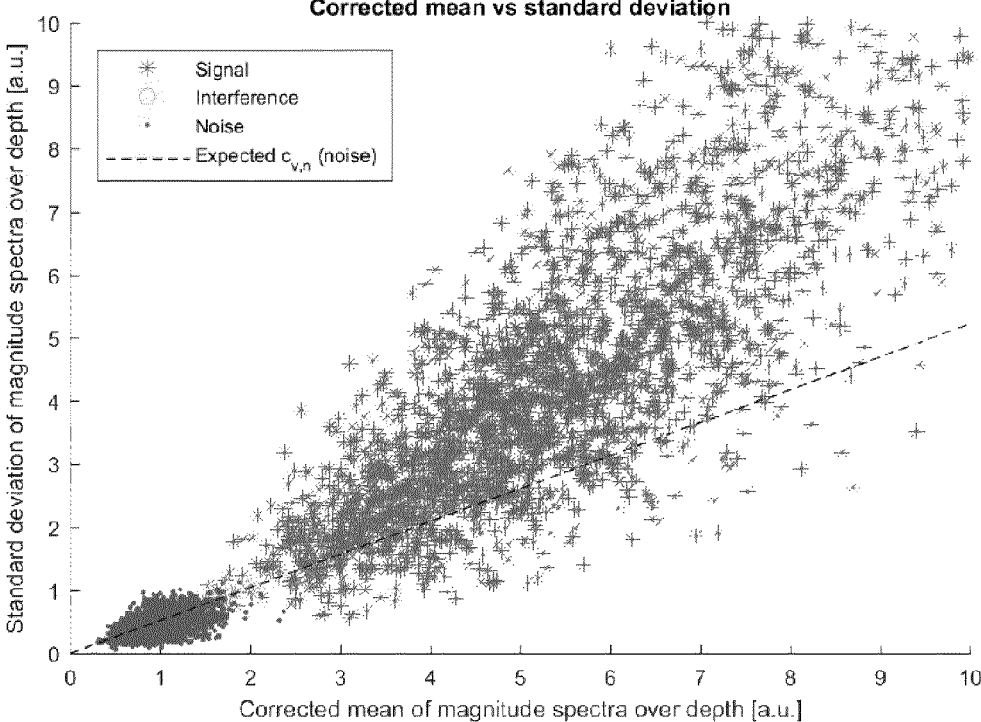
FIG. 7. Corrected mean versus original standard deviation. For pixels classified as interference, the mean is reduced: interference-affected data points from FIG. 5 are effectively shifted to the left in this graph towards the dashed black line representing the statistical noise relations.
Figure 8:
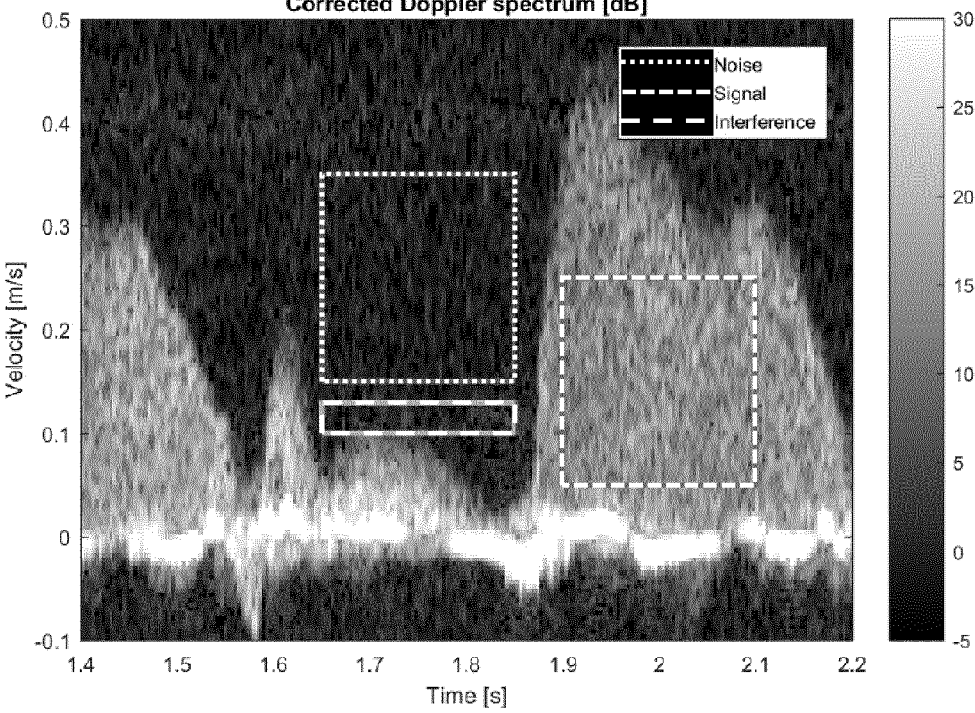
FIG. 8. Corrected Doppler spectrum.
Figure 9:
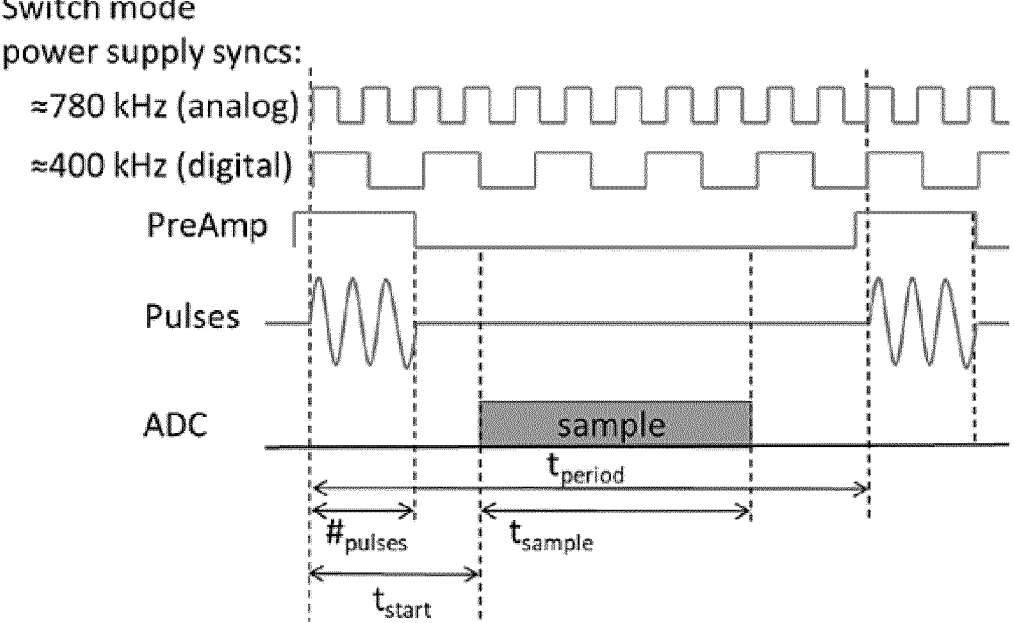
FIG. 9. Schematic view of timing of analog and digital switch-mode power supplies (top two rows) in relation to the flow acquisition pulses (denoted with "Pulses").
Figure 10:
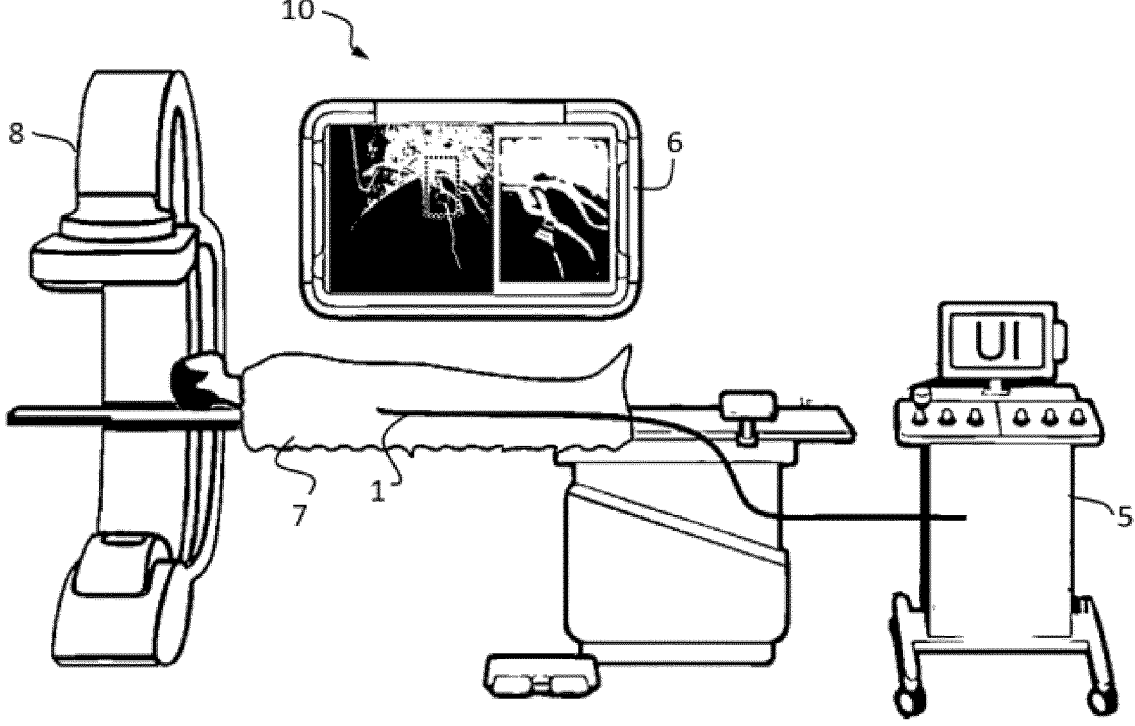
FIG. 10. Exemplary system according to the invention.

The invention claimed is:

1. An apparatus for flow measurement in a vessel, comprising a processor configured to:

obtain a plurality of ultrasound signals from an ultrasound transducer of an interventional device, wherein the plurality of ultrasound signals originate from a range of depths within the vessel with respect to the ultrasound transducer;

ascertain from the plurality of ultrasound signals, flow velocity spectra over the range of depths;

detect a measure for similarity or variation of the flow velocity spectra over the range of depths; and obtain a composite flow velocity spectrum over the range of depths within the vessel by suppressing interference components from the flow velocity spectra based on the measure for similarity or variation of the flow velocity spectra over the range of depths.

2. The apparatus of claim 1, further comprising a display, or an audio device, and wherein the processor is configured to output to the display the composite flow velocity spectrum over the range of depths, or a parameter derived from it;

or wherein the processor is configured to output to the audio device an audio signal representing the composite flow velocity spectrum over the range of depths.

3. The apparatus of claim 2, wherein the processor is further configured to:

identify as flow signal components, portions of the flow velocity spectra having a relatively lower value of the measure for similarity over the range of depths; and identify as the interference components, portions of the flow velocity spectra having a relatively higher value of the measure for similarity over the range of depths;

or:

identify as flow signal components, portions of the flow velocity spectra having a relatively higher value of the measure for variation over the range of depths; and identify as the interference components, portions of the flow velocity spectra having a relatively lower value of the measure for variation over the range of depths.

4. The apparatus of claim 1, wherein the processor is configured to detect the measure for similarity or variation of the flow velocity spectra over the range of depths by performing a statistical analysis on the flow velocity spectra, or by calculating a value of a correlation metric for the flow velocity spectra, or by calculating a value of a coherence metric for the flow velocity spectra.

5. The apparatus of claim 4, wherein the processor is configured to detect the measure for variation of the flow velocity spectra over the range of depths by performing a statistical analysis on the flow velocity spectra, and wherein the performing a statistical analysis on the flow velocity spectra comprises:

calculating mean and/or standard deviation and/or variance values for the flow velocity spectra over the range of depths to provide the measure for the variation of the flow velocity spectra over the range of depths.

6. The apparatus of claim 5, wherein the performing a statistical analysis on the flow velocity spectra comprises calculating mean and standard deviation values for the flow velocity spectra over the range of depths; and wherein the processor is configured to:

identify as flow signal components, portions of the flow velocity spectra having relatively higher values of the measure for the variation of the flow velocity spectra over the range of depths; and identify as the interference components, portions of the flow velocity spectra having relatively lower values of the measure for the variation of the flow velocity spectra over the range of depths; and wherein the measure for the variation of the flow velocity spectra over the range of depths is provided by the standard deviation values, or by a ratio ($c_v$) of the standard deviation values to the corresponding mean values; and wherein the relatively higher values of the measure for the variation of the flow velocity spectra over the range of depths, and the relatively lower values of the measure for the variation of the flow velocity spectra over the range of depths are evaluated with respect to a classification threshold.

7. The apparatus of claim 6, wherein the classification threshold is calculated based on a ratio ($c_{vn}$) of a standard deviation ($\sigma$) to a mean value ($\mu$) for an expected noise spectrum.

8. The apparatus of claim 6, wherein the measure for the variation of the flow velocity spectra over the range of depths is provided by the ratio ($c_v$) of the standard deviation values to the corresponding mean values; and wherein the processor is configured to:

identify as the flow signal components, the portions of the flow velocity spectra having relatively higher values of the ratio ($c_v$) of the standard deviation value to the mean value; and identify as the interference components, the portions of the flow velocity spectra having relatively lower values of the ratio ($c_v$) of the standard deviation value to the mean value.

9. The apparatus of claim 6, wherein the measure for the variation of the flow velocity spectra over the range of depths is provided by the standard deviation values; and wherein the processor is further configured to:

identify as flow signal components, portions of the flow velocity spectra having a relatively lower value of the standard deviation at the corresponding mean value; and identify as the interference components, portions of the flow velocity spectra having a relatively higher value of the standard deviation at the corresponding mean value; and wherein the relatively higher value of the standard deviation, and the relatively lower value of the standard deviation, are evaluated at the corresponding mean value with respect to a classification threshold; and wherein the classification threshold is calculated based on a ratio ($c_{vn}$) of the standard deviation ($\sigma$) to the mean value ($\mu$) for an expected noise spectrum, and the corresponding mean value.

10. The apparatus of claim 9, wherein the classification threshold comprises an error margin, and wherein the error margin reduces a value of the classification threshold, and wherein the error margin is calculated based on: the ratio ($c_{vn}$) of the standard deviation ($\sigma$) to the mean value ($\mu$) for the expected noise spectrum, and the corresponding mean value ($\mu_s(t, f)$, and an offset value $\Delta\sigma$ for the standard deviation and/or a gradient multiplication factor, k; and wherein the classification threshold $\tilde{\sigma}_{Th}$(t, f) comprising the error margin is calculated for the portion of the flow velocity spectra at a time, t, and a frequency, f, using the equation:

$$\tilde{\sigma}_{Th}(t, f) = k \cdot (c_{vn} \cdot \tilde{\mu}_S(t, f) - \Delta\sigma)$$

wherein ($\tilde{\mu}_s$(t, f) represents the corresponding mean value of the spectrum at the time, t, and the frequency, f.

11. The apparatus of claim 1, wherein the suppressing interference components from the flow velocity spectra based on the measure for similarity or variation, comprises:

replacing the interference components in the flow velocity spectra with expected corresponding noise components; or subtracting the interference components from the flow velocity spectra; or wherein the apparatus further comprises a display, and wherein the processor is further configured to output to the display the composite flow velocity spectrum as an image comprising a plurality of pixels, and wherein pixels in the displayed image have intensity values that are determined by replacing pixels in the flow velocity spectra that represent interference components with interpolated values that are calculated from neighbouring positions in time and frequency in the composite flow velocity spectrum that do not represent interference components.

12. The apparatus of claim 1, wherein:

the ascertaining flow velocity spectra further comprises filtering the plurality of ultrasound signals in the time domain or in the frequency domain; and/or wherein the processor is configured to detect the measure for similarity or variation of the flow velocity spectra by performing a statistical analysis on the flow velocity spectra; and wherein the processor is further configured to smooth the values obtained from the statistical analysis prior to detecting the measure for similarity or variation of the flow velocity spectra.

13. The apparatus according to claim 1, further comprising a display, and wherein the processor is configured to:

estimate, from the composite flow velocity spectrum, a value of one or more of: an instantaneous peak velocity, IPV, an average peak velocity, APV, and a coronary flow reserve, CFR; and output, to the display, the respective value(s).

14. An apparatus for flow measurement in a vessel, the apparatus comprising a processor configured to:

obtain a plurality of ultrasound signals from an ultrasound transducer of an interventional device, wherein the plurality of ultrasound signals originate from a range of depths within the vessel with respect to the ultrasound transducer;

ascertain from the plurality of ultrasound signals, flow velocity spectra over the range of depths;

detect a measure for similarity or variation of the flow velocity spectra over the range of depths; and identify one or more interference components from the flow velocity spectra based on the measure for similarity or variation of the flow velocity spectra over the range of depths.

15. The apparatus of claim 14, wherein the plurality of ultrasound signals represent backscattered ultrasound radiation originating from moving particles in blood in the vessel at the plurality of depths, the backscattered ultrasound radiation being backscattered in response to ultrasound radiation emitted by the ultrasound transducer.

\* \* \* \* \*